United States Patent
Petersen et al.

(10) Patent No.: US 6,258,842 B1
(45) Date of Patent: Jul. 10, 2001

(54) METHOD FOR THE PREPARATION OF CITALOPRAM

(75) Inventors: Hans Petersen, Vanløse; Peter Bregnedal, Allerød; Klaus Peter Bogeso, Hørsholm, all of (DK)

(73) Assignee: H. Lundbeck, A/S, Valby-Copenhagen (DK)

( * ) Notice: Subject to any disclaimer, the term of this patent is extended or adjusted under 35 U.S.C. 154(b) by 0 days.

(21) Appl. No.: 09/564,365

(22) Filed: Apr. 28, 2000

Related U.S. Application Data

(63) Continuation of application No. PCT/DK97/00513, filed on Nov. 11, 1997.

(51) Int. Cl.⁷ .......................... A61K 31/34; C07D 307/81
(52) U.S. Cl. ..................... 514/469; 549/467; 564/315; 564/316
(58) Field of Search ............... 549/467; 514/469; 564/315, 316

(56) References Cited

U.S. PATENT DOCUMENTS

| | | | |
|---|---|---|---|
| 3,467,675 | 9/1969 | Petersen et al. | 260/346.2 |
| 4,136,193 | 1/1979 | Bøgesø et al. | 424/285 |

FOREIGN PATENT DOCUMENTS

| | | |
|---|---|---|
| 0 171 943 A1 | 2/1986 | (EP) . |
| WO 92/22554 | 12/1992 | (WO) . |
| WO 98/19511 | 5/1998 | (WO) . |

OTHER PUBLICATIONS

Petersen, H. et al "method for the preparation of citalopram" CA 129:16050, 1998.*

Bigler, Allan J. et al., "Quantitative structure–activity relationships in a series of selective 5–HT uptake inhibitors," *Eur. J. Med. Chem.* 12, 3: 289–295 (May–Jun. 1997).

Perregaard, Jens et al., "α Ligands with Subnanomolar Affinity and and Preference for the σ₂ Binding Site. 1. 3–α Aminoalkykl)–1*H*–indoles," *J. Med. Chem.* 38: 1998–2008 (1995).

Moltzen, Ejner K. et al., "α Ligands with Subnanomolar Affinity and Preference for the σ₂ Binding Site. 2. Spiro–Joined Benzofuran, Isobenzofuran, and Benzopyran Piperidines, " *J. Med. Chem.* 38: 2009–2017 (1995).

\* cited by examiner

*Primary Examiner*—Amelia Owens
(74) *Attorney, Agent, or Firm*—Darby & Darby

(57) ABSTRACT

A method for the preparation of citalopram is described comprising reaction of a compound of Formula (IV) wherein $R^1$ is H or $C_{1-6}$alkylcarbonyl successively with a Grignard reagent of 4-halogen-fluorophenyl and a Grignard reagent of 3-halogen-N,N-dimethylpropylamine, effecting ring closure of the resulting compound of Formula (IV) and converting the resulting 1,3-dihydroisobenzofuran compound to the corresponding 5-cyano derivative, i.e. citalopram.

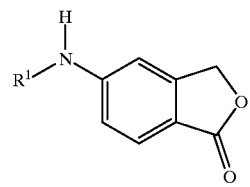

(IV)

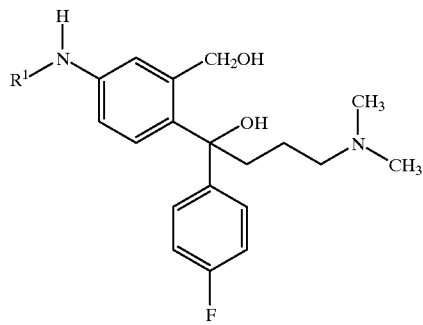

(VI)

18 Claims, No Drawings

METHOD FOR THE PREPARATION OF CITALOPRAM

This is a continuation of International Application No. PCT/DK97/00513, filed Nov. 11, 1997.

The present invention relates to a method for the preparation of the well known antidepressant drug citalopram and intermediates used in the process.

BACKGROUND OF THE INVENTION

Citalopram is a well known antidepressant drug that has now been on the market for some years and has the following structure:

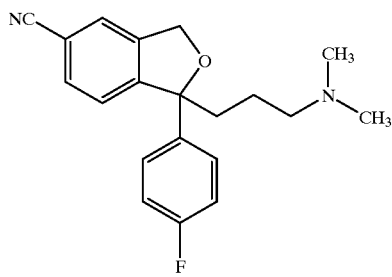

Formula I

It is a selective, centrally active serotonin (5-hydroxytryptamine; 5-HT) reuptake inhibitor, accordingly having antidepressant activities. The antidepressant activity of the compound has been reported in several publications, ea. J. Hyttel, *Prog. Neuro-Psychopharmacol. & Biol. Psychiat.*, 1982, 6, 277–295 and A. Gravem, *Acta Psychiatr. Scand.*, 1987, 75, 478–486. The compound has further been disclosed to show effects in the treatment of dementia and cerebrovascular disorders, EP-A 474580.

Citalopram was first disclosed in DE 2,657,271 corresponding to U.S. Pat. No. 4,136,193. This patent publication describes the preparation of citalopram by one method and outlines a further method which may be used for preparing citalopram.

According to the process described, the corresponding 1-(4-fluorophenyl)-1,3-dihydro-5-isobenzofurancarbonitrile is reacted with 3-(N,N-dimethylamino)propyl-chloride in the presence of methylsulfinylmethide as condensing agent. The starting material was prepared from the corresponding 5-bromo derivative by reaction with cuprous cyanide.

According to the method, which is only outlined in general terms, citalopram may be obtained by ring closure of the compound:

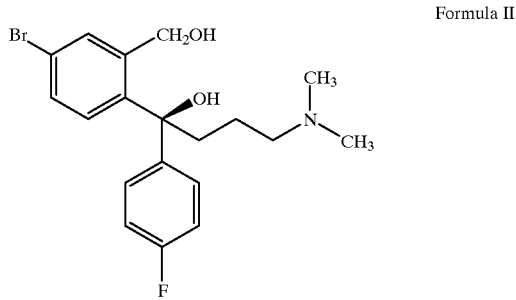

Formula II in the presence of a dehydrating agent and subsequent exchange of the 5-bromo group with cuprous cyanide. The starting material of Formula II is obtained from 5-bromophthalide by two successive Grignard reactions, i.e. with 4-fluorophenyl magnesium chloride and N,N-dimethylaminopropyl magnesium chloride, respectively.

A new and surprising method and an intermediate for the preparation of citalopram were described in U.S. Pat. No. 4,650,884 according to which an intermediate of the formula

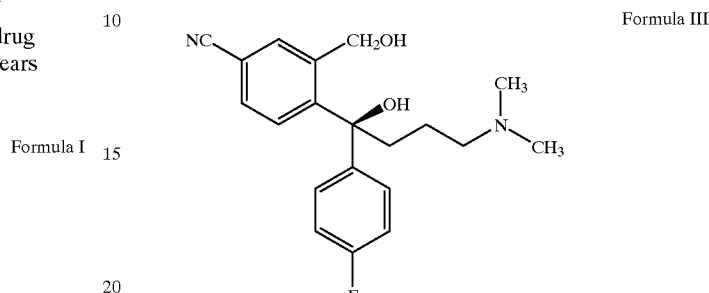

Formula III is subjected to a ring closure reaction by dehydration with strong sulfuric acid in order to obtain citalopram. The intermediate of Formula III was prepared from 5-cyanophthalide by two successive Grignard reactions, i.e. with 4-fluorophenyl magnesium halogenide and N,N-dimethylaminopropyl magnesium halogenide, respectively.

Finally, methods of preparing the individual enantiomers of citalopram are disclosed in U.S. Pat. No 4,943,590 from which it also appears that the ring closure of the intermediate of Formula III may be carried out via a labile ester with a base.

It has now, surprisingly, been found that citalopram may be manufactured by a novel favourable and safe procedure using convenient starting materials.

SUMMARY OF THE INVENTION

Accordingly, the present invention relates to a novel method for the preparation of citalopram comprising the steps of:

a) reacting a compound of Formula IV

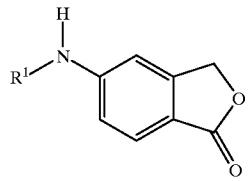

Formula IV wherein $R^1$ is H or $C_{1-6}$ alkylcarbonyl, with a Grignard reagent of 4-halogen-fluorophenyl;

b) reacting the resulting compound of formula V

Formula V

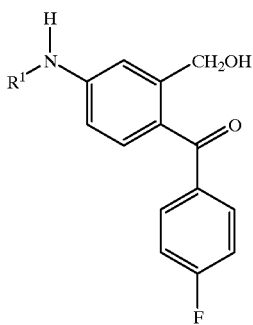

wherein $R^1$ is as defined above, with a Grignard reagent of 3-halogen-N,N-dimethylpropylamine;

c) effecting ring closure of the resulting compound of Formula VI

Formula VI

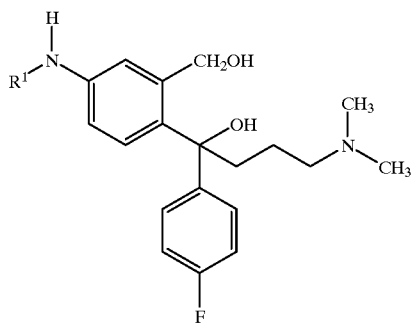

wherein $R^1$ is as defined above, and d) converting the resulting compound of Formula VII Formula VII

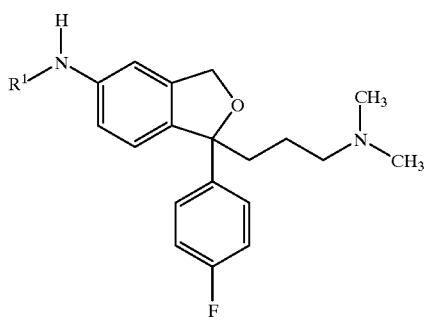

wherein $R^1$ is as defined above, into the corresponding 5-cyano derivative, i.e. citalopram, which is isolated as the base or a pharmaceutically acceptable salt thereof.

In another aspect, the present invention provides the novel intermediates of Formula V.

In a further aspect, the present invention provides the novel intermediates of Formula VI.

In a further aspect, the present invention provides the novel intermediates of Formula VII.

In yet another aspect, the present invention relates to an antidepressant pharmaceutical composition comprising citalopram manufactured by the process of the invention.

Throughout the specification and claims, $C_{1-6}$ alkyl refers to a branched or unbranched alkyl group having from one to six carbon atoms inclusive, such as methyl, ethyl, 1-propyl, 2-propyl, 1-butyl, 2-butyl, 2-methyl-2-propyl, 2,2-dimethyl-1-ethyl and 2-methyl-1-propyl.

Grignard reagents of 4-halogen-fluorophenyl that may be used in step a) are the magnesium halogenides, such as the chloride, bromide or iodide. Preferably the magnesium bromide is used. Grignard reagents of 3-halogen-N,N-dimethylpropylamine that may be used are the magnesium halogenides, such as the chloride, bromide or iodide, preferably the magnesium bromide. Preferably the two reactions are performed successively without isolation of the intermediate.

The ring closure of the compound of Formula VI may be effected by an acid or when $R^1$ is $C_{1-6}$ alkylcarbonyl, it may alternatively be carried out via a labile ester with a base. Acidic ring closure is performed by an inorganic acid, such as a sulfuric or phosphoric acid, or an organic acid, such as methylsulfonic, p-toluenesulfonic or trifluoroacetic acid. The basic ring closure is performed via a labile ester, such as the methane sulfonyl, p-toluene sulfonyl, 10-camphorsulfonyl, trifluoroacetyl or trifluoromethanesulfonyl ester with addition of a base, such as triethyl amine, dimethylaniline or pyridine. The basic reaction is performed in an inert solvent, preferably with cooling, in particular about 0° C. and is preferably carried out by a one-pot procedure, i.e. with esterification and simultaneous addition of the base.

When $R^1$ is H, the conversion of $R^1$—NH— into cyano is preferably performed by diazotation and followed by reaction with $CN^{31}$. Most preferably $NaNO_2$ and CuCN and/or NaCN are used. When $R^1$ is $C_{1-6}$ alkylcarbonyl, it is initially subjected to hydrolysis thereby obtaining the corresponding compound wherein $R^1$ is H which is the converted as described above. The hydrolysis may be performed either in acidic or basic environment.

The process of the invention may be carried out with or without isolation of the intermediates.

The process of the invention may also be used to prepare the active (S)-enantiomer of citalopram. In that case, the compound of formula VI is separated into the optically active enantiomers by a procedure analogous to the one described in U.S. Pat. No. 4,943,590 thereby obtaining the (S)-enantiomer of the compound of formula VI which is used in the ring closure reaction in step c). Accordingly, the individual enantiomers of the intermediates of formulas VI and VII, respectively, are embraced by the formulas.

Other reaction conditions, solvents, etc. are conventional conditions for such reactions and may easily be determined by a person skilled in the art.

The starting material of formula IV wherein $R^1$ is H is commercially available and may be prepared by known procedures (Tirouflet, J.; Bull. Soc. Sci. Bretagne 26, 1959, 35) and compounds wherein $R^1$ is acyl may be prepared from the amino compound ($R^1$ is H) by conventional acylation.

In one embodiment of the invention, $R^1$ is $C_{1-6}$ alkylcarbonyl, in particular methyl-, ethyl-, propyl-, or butylcarbonyl.

In another embodiment of the invention $R^1$ is H.

The compound of general Formula I may be used as the free base or as a pharmacologically acceptable acid addition salt thereof. As acid addition salts, such salts formed with organic or inorganic acids may be used. Exemplary of such organic salts are those with maleic, fumaric, benzoic, ascorbic, succinic, oxalic, bis-methylenesalicylic, methanesulfonic, ethanedisulfonic, acetic, propionic, tartaric, salicylic, citric, gluconic, lactic, malic, mandelic, cinnamic, citraconic, aspartic. stearic, palmitic. itaconic, glycolic, p-amino-benzoic, glutamic, benzene sulfonic and theophylline acetic acids as well as the 8-halotheophyllines, for example 8-bromotheophylline. Exemplary of such inorganic salts are those with hydrochloric, hydrobromic, sulfuric, sulfamic, phosphoric and nitric acids.

The acid addition salts of the compounds may be prepared by methods known in the art. The base is reacted with either the calculated amount of acid in a water miscible solvent, such as acetone or ethanol, with subsequent isolation of the salt by concentration and cooling, or with an excess of the acid in a water immiscible solvent, such as ethylether, ethylacetate or dichloromethane, with the salt separating spontaneously.

The pharmaceutical compositions according to the invention may be administered in any suitable way and in any suitable form, for example orally in the form of tablets, capsules, powders or syrups, or parenterally in the form of usual sterile solutions for injection.

The pharmaceutical formulations of the invention may be prepared by conventional methods in the art. For example, tablets may be prepared by mixing the active ingredient with ordinary adjuvants and/or diluents and subsequently compressing the mixture in a conventional tabletting machine. Examples of adjuvants or diluents comprise: Corn starch, potato starch, talcum, magnesium stearate, gelatine, lactose, gums, and the like. Any other adjuvant or additive colourings, aroma, preservatives etc. may be used provided that they are compatible with the active ingredients.

Solutions for injections may be prepared by solving the active ingredient and possible additives in a part of the solvent for injection, preferably sterile water, adjusting the solution to the desired volume, sterilization of the solution and filling in suitable ampules or vials. Any suitable additive conventionally used in the art may be added, such as tonicity agents, preservatives, antioxidants, etc.

EXAMPLES

The process of the invention is farther illustrated by the following Examples.

Example 1

4-Dimethylamino-1-(4-amino-2-hydroxymetlylphenyl)-1-(4-fluorophenyl)butan-1-ol.

A solution of 4-fluorophenylmagnesium bromide prepared from 4-fluorobromobenzene (116 g, 0.66 mole) and magnesium turnings (20 g, 0.8 mole) in dry THF (500 ml), is added dropwise to a suspension of 5-amino-phthalide (30 g, 0.2 mole) in dry THF (500 ml). The temperature is kept below 5° C. After the addition is completed, the reaction mixture is stirred for 0.5 hour at room temperature.

A second Grignard solution prepared from 3-dimethylaminopropyl chloride (25 g, 0.2 mole) and magnesium turnings (6 g, 0.25 mole) in dry THF (150 ml) is added to the reaction mixture. The temperature is kept below 5° C. during the addition. Stirring is continued for 0.5 hour, then stopped and left overnight at ambient temperature.

The reaction mixture is broken with ice water (1000 ml) and acetic acid (60 g). THF is evaporated off in vacuo. The aqueous phase is washed with ethyl acetate (2×200 ml). To the aqueous phase is added $NH_4OH$ to give a final pH of 9. The aqueous layer is extracted with ethyl acetate (2×200 ml), and the organic phase is filtered and washed with water (100 ml). Evaporation of the solvents in vacuo leaves the title compound (38.8 g, 58%) as an oil.

$^1$H NMR ($CDCl_3$, 500 MHz): 1.45–1.55 (1H, m), 1.65–1.75 (1H, m), 2.2 (6H,s), 2.27 (1H, m),2.33 (2H, m), 2.43 (1H, m) 3.6–3.7 (2H, $NH_2$), 3.97 (1H, d J=12.5 Hz) 4.25 (1H, J=12.5 Hz), 6.58 (1H, d, J=8 Hz), 6.62 (1H, s), 6.95 (2H, t, J=8.5 Hz), 7.25 (1H, d, J=8 Hz), 7.45 (2H, dt, J=1.2 Hz J=8.5 Hz).

5-Amino-1-(3-dimethylaminopropyl)-1-(4-fluorophenyl)-1,3-dihydroisobenzofuran.

Crude 4-dimethylamino-1-(4-amino-2-hydroxymethylphenyl)-1-(4-fluorophenyl)butan-1-ol. is dissolved in $H_3PO_4$ (60%, 140 g) and heated to 80° C. for 2 hours. The reaction mixture is poured on ice water (1000 ml). $NH_4OH$ is added to give a final pH of 9. The aqueous layer is extracted with ethyl acetate (2×200 ml). The combined organic phase is filtered, washed with water (100 ml) and dried ($MgSO_4$, 10 g). The solvent is evaporated in vacuo. The title compound is obtained as an oil.

$^1$H NMR ($CDCl_3$, 250 MHz): 1.3–1.5 (2H, m), 2.05–2.3 (10 H, s+m), 3.6–3.7 (2H, $NH_2$)5.0 (1H, s), 6.45 (1H, d, J=1.8 Hz), 6.55 (1H, dd, J=8 Hz J=1.8 Hz), 6.95 (2H, t, J=8.5 Hz)7.05 (1H, d, J=8 Hz), 7.45 (2H, dt, J=1.2 Hz J=8.5 Hz).

1-(3-Dimethylaminopropyl)-1-(4-fluorophenyl)-1,3-dihydroisobenzofuran-5-carbonitrile.

5-Amino-1-(3-dimethylaminopropyl)-1-(4-fluorophenyl)-1,3-dihydroisobenzofuran (18 g, 0.06 mole) is dissolved in water (100 ml) and $H_2SO_4$(8 ml). $NaNO_2$(4.1 g, 0.06 mole) is dissolved in water (20 ml) and added dropwise below 5° C. The diazotised solution is stirred for 0.5 hour at 0–5° C. pH is brought to 6.5 by adding a saturated solution of $Na_2CO_3$. This solution is added to a mixture of water (100 ml) and toluene (120 ml) containing CuCN(6 g, 0.067 mole) and NaCN (10 g, 0.2 mole) at 50–60C°. Stirring is continued for 0.5 hour. The phases are separated and the aqueous phase is further extracted with toluene (100 ml). The combined organic phase is washed with NaCN(10% aq., 2×50 ml). The solvent is removed in vacuo and the residue is chromatograhed on silica gel (ethyl acetate: n-heptane: triethylamine; 85:10:5 ) to give the title compound (6 g, 32%) as an oil.

$^1$H NMR ($CDCl_3$, 250 MHz): 1.35 (1H, m), 1.45 (1H, m),2.1(6H,s), 2.15–2.2 (4H, m), 5.12(1H, d, J=12.5 Hz), 5.18 (1H, d, J=12.5 Hz),7.00(2H, t, J=8.5Hz), 7.4 (2H, t, J=8.5 Hz), 7.45 (1H, d, J=7.5 Hz),7.5(1H, s),7.58(1H, d, J=7.5 Hz).

Example 2

4-Dimethylamino-1-(4-acetylamino-2-hydroxymethylphenyl)-1-(4-fluorophenyl)butan-1-ol.

A solution of 4-fluorophenylmagnesium bromide prepared from 4-fluorobromobenzene (11.6 g, 0.067 mole) and magnesium turnings (2 g, 0.08 mole) in dry THF (50 ml), is added dropwise to a suspension of 5-acetylamino-phthalide (5 g,0.03 mole) in dry THF (50 ml). The temperature is kept below 5 ° C. After the addition is completed, the reaction mixture is stirred for 0.5 hour at room temperature.

A second Grignard solution prepared from 3-dimethylaminopropyl chloride (3.7 g, 0.03 mole) and magnesium turnings (0.87 g, 0.036 mole) in dry THF (15 ml) is added to the reaction mixture. The temperature is kept below 5° C. during the addition. Stirring is continued for 0.5 hour, then stopped and left overnight at ambient temperature. The reaction mixture is broken with ice water (100 ml) and acetic acid (6 g). THF is evaporated off in vacuo. The aqueous phase is washed with ethyl acetate (2×50 ml). To the aqueous phase is added $NH_4OH$ to give a final pH of 9. The aqueous layer is extracted with ethyl acetate (2×50 ml), and the organic phase is filtered and washed with water (50 ml). Evaporation of the solvents in vacuo leaves the title compound (6.6 g, 63 %) as an oil.

$^1$H NMR (DMSO-$d_6$, 500 MHz):1.15–1.22 (1H, m), 1.40–1.50 (1H, m), 2.02(9H, s+s), 2.05 ($^1$H, m), 2.13(2H, m),2.20(1H, m),3.95(1H, d J=12.5 Hz) 4.48(1H, d J=12.5 Hz), 7.05 (2H,t,J=8.5 Hz),7.14(2H, dd J=8.5 Hz J=1.2 Hz),7.47(1H, d J=8 Hz), 7.5(1H, d J=8.5 Hz).

What is claimed is:

1. A method for the preparation of citalopram comprising the steps of
a) reacting a compound of Formula IV

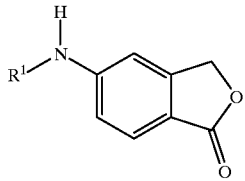

wherein $R^1$ is H or $C_{1-6}$ alkylcarbonyl with a Grignard reagent of 4-halogen-fluorophenyl;
b) reacting the resulting compound of Formula V

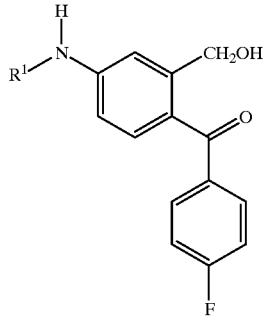

wherein $R^1$ is as defined above, with a Grignard reagent of 3-halogen-N,N-dimethylpropyl-amine;
c) effecting ring closure of the resulting compound of Formula VI

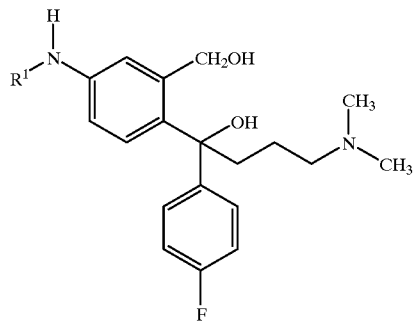

wherein $R^1$ is as defined above, and
d) converting the resulting compound of Formula VII

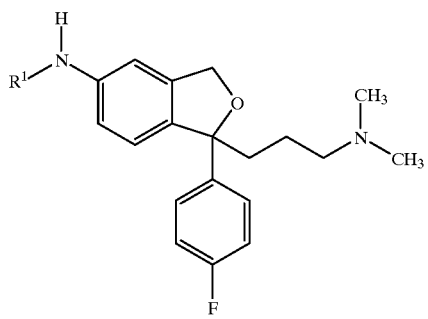

wherein $R^1$ is as defined above, into citalopram, which is isolated as a base or a pharmaceutically acceptable salt thereof.

2. The method of claim 1 wherein $R^1$ is H.

3. The method of claim 1 wherein $R^1$ is $C_{1-6}$ alkylcarbonyl.

4. The method of claim 3 wherein $C_{1-6}$ alkyl is methyl, ethyl, propyl or butyl.

5. The method of claim 1 wherein the Grignard reagents of steps (a) and (b) are magnesium halogenides.

6. The method of claim 5 wherein the Grignard reagent of step a) is the magnesium bromide.

7. The method of claim 5 wherein the Grignard reagent of step b) is the magnesium chloride.

8. The method of claim 1 wherein the ring closure of the compound of Formula VI is effected by acidic ring closure performed by an inorganic acid or an organic acid.

9. The method of claim 8 wherein said acidic ring closure is performed by an inorganic acid selected from the group consisting of sulfuric acid and phosphoric acid.

10. The method of claim 8 wherein said acidic ring closure is performed by an organic acid selected from the group consisting of methylsulfonic, p-toluenesulfonic and trifluoroacetic acid.

11. The method of claim 3 wherein the ring closure of the compound of Formula VI is performed by a basic ring closure via a labile ester, optionally with simultaneous esterification and addition of base.

12. The method of claim 11 wherein the labile ester is selected from the group consisting of methane sulfonyl, p-toluene sulfonyl, 10-camphorsulfonyl, trifluoroacetyl and trifluoromethanesulfonyl ester and the base is selected from the group consisting of triethyl amine, dimethylaniline and pyridine.

13. The method of claim 2 wherein the conversion of the group $R^1$—NH— into cyano is performed by diazotation followed by reaction with $CN^-$.

14. The method of claim 3 wherein the conversion of the group $R^1$—NH— to cyano is performed by hydrolysis of the $C_{1-6}$ alkylcarbonyl amino group $R^1$—NH— to the corresponding amino group wherein $R^1$ is H, followed by diazotation and reaction with $CN^-$.

15. The process of claim 1, wherein the compound of formula VI is separated into optically active enantiomers, thereby obtaining the (S)-enantiomer, before step (c).

16. A compound of Formula V

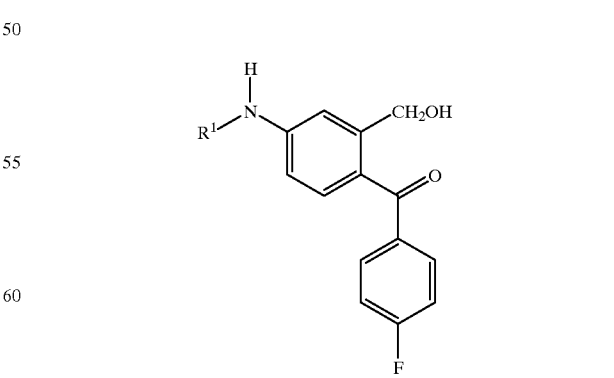

wherein $R^1$ is H or $C_{1-6}$ alkylcarbonyl.

17. A compound of Formula VI
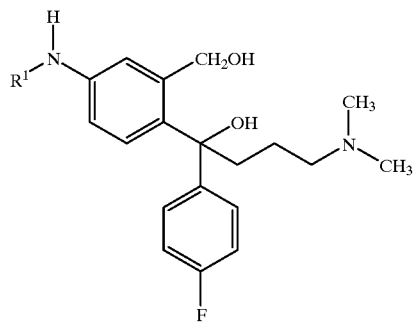
wherein $R^1$ is H or $C_{1-6}$ alkylcarbonyl.
18. A compound of Formula VII
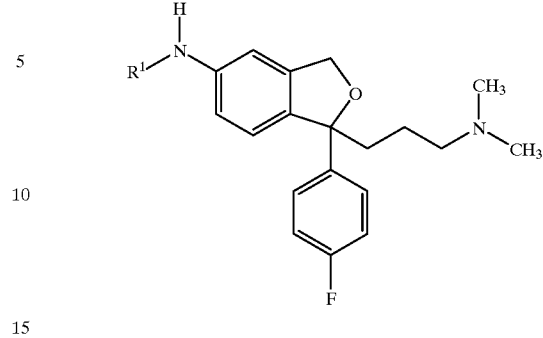
wherein $R^1$ is H or $C_{1-6}$ alkylcarbonyl.
* * * * *